US012491349B2

(12) United States Patent
Kim

(10) Patent No.: US 12,491,349 B2
(45) Date of Patent: Dec. 9, 2025

(54) INTERNAL DRAINAGE CATHETER FOR ASCITES DRAINAGE

(71) Applicant: WABE-TREE CO., LTD., Gyeongsangnam-do (KR)

(72) Inventor: Il Hwan Kim, Busan (KR)

(73) Assignee: WABE-TREE CO., LTD., Gyeongsangnam-Do (KR)

( * ) Notice: Subject to any disclaimer, the term of this patent is extended or adjusted under 35 U.S.C. 154(b) by 130 days.

(21) Appl. No.: 18/037,362

(22) PCT Filed: May 25, 2022

(86) PCT No.: PCT/KR2022/007397

§ 371 (c)(1),
(2) Date: May 17, 2023

(87) PCT Pub. No.: WO2022/260316

PCT Pub. Date: Dec. 15, 2022

(65) Prior Publication Data

US 2024/0001093 A1 Jan. 4, 2024

(30) Foreign Application Priority Data

Jun. 7, 2021 (KR) ........................ 10-2021-0073213

(51) Int. Cl.
*A61M 27/00* (2006.01)
*A61M 39/24* (2006.01)

(52) U.S. Cl.
CPC .......... *A61M 27/008* (2013.01); *A61M 39/24* (2013.01); *A61M 2210/1017* (2013.01); *A61M 2210/1085* (2013.01)

(58) Field of Classification Search
CPC .......... A61M 39/24; A61M 2025/0076; A61M 25/0075; A61M 2210/1017; A61M 2210/1085; A61M 39/08; A61M 2039/242; A61M 27/002; A61M 25/0017; A61M 25/007; A61M 25/04; A61M 2025/0078; A61M 2205/0266; A61M 27/00–008; A61M 39/00–288;
(Continued)

(56) References Cited

U.S. PATENT DOCUMENTS 9,364,647 B1 * 6/2016 Beckman ............ A61M 27/006
2003/0163204 A1 * 8/2003 Rix ........................... A61F 2/04 604/8
(Continued)

FOREIGN PATENT DOCUMENTS

CN 106924864 A 7/2017
KR 20-0429409 Y1 10/2006
(Continued)

OTHER PUBLICATIONS

International Search Report for PCT/KR2022/007397 mailed on Sep. 15, 2022.

*Primary Examiner* — Susan S Su
(74) *Attorney, Agent, or Firm* — The PL Law Group, PLLC

(57) ABSTRACT

An internal drainage catheter for ascites drainage according to an embodiment has an improved structure so as to allow ascites in a peritoneal cavity to be discharged in urine via a bladder and ensure significant fixation force to a bladder wall based on which the peritoneal cavity and the bladder are separated from each other.

5 Claims, 11 Drawing Sheets

(58) Field of Classification Search
CPC .. A61M 2039/0009–282; A61F 2/2476; A61F 2/94
See application file for complete search history.

(56) References Cited

U.S. PATENT DOCUMENTS

| | | | | |
|---|---|---|---|---|
| 2007/0276466 | A1* | 11/2007 | Lavelle | A61F 2/04 623/1.22 |
| 2009/0048654 | A1* | 2/2009 | Chmura | A61M 27/008 623/1.11 |
| 2010/0070047 | A1 | 3/2010 | Smouse | |
| 2013/0006162 | A1* | 1/2013 | Quintero | A61M 25/04 604/8 |
| 2014/0012180 | A1 | 1/2014 | Levin et al. | |
| 2014/0277096 | A1 | 9/2014 | Richter et al. | |

FOREIGN PATENT DOCUMENTS

| | | | |
|---|---|---|---|
| KR | 10-1671612 | B1 | 11/2016 |
| KR | 10-2020-0126046 | A | 11/2020 |

* cited by examiner

INTERNAL DRAINAGE CATHETER FOR ASCITES DRAINAGE

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2022/007397, filed May 25, 2022, which claims priority to the benefit of Korean Patent Application No. 10-2021-0073213 filed in the Korean Intellectual Property Office on Jun. 7, 2021, the entire contents of which are incorporated herein by reference.

BACKGROUND

1. Technical Field

The present invention relates to an internal drainage catheter for ascites drainage, and more particularly, to an internal drainage catheter for ascites drainage having an improved structure so as to allow ascites in a peritoneal cavity to be discharged in urine via a bladder and ensure a significant fixation force to the bladder wall based on which the peritoneal cavity and the bladder are separated from each other.

2. Background Art

In liver cirrhosis or peritoneal disseminated diseases (peritoneal carcinomatosis of cancer: when stomach cancer/colon cancer/pancreatic cancer/ovarian cancer is metastasized to the peritoneum), ascites symptoms occur in which water fills the inside of the peritoneal cavity. When ascites symptoms worsen, a patient is accompanied by symptoms such as discomfort, pain, and mobility problems due to abdominal distension.

In this case, as well shown in FIGS. 1 and 2, repetitive ascites punctures (a procedure in which ascites is removed from the abdomen by repeatedly stabbing the abdomen with a needle) are required to improve symptoms. However, because the improvement of the symptoms does not last long, a patient is repeatedly subjected to multiple punctures at regular intervals (about 2 to 3 liters of ascites are cultured per procedure). This procedure causes a lot of discomfort, such as pain, because the abdomen must be pierced into the peritoneum with a thick needle. As the number of repetitive ascites punctures increases, the intestine may be punctured, causing intestinal perforation, or many complications such as bleeding and infection are accompanied.

There is also a catheter insertion through the intestinal wall (PCD: percutaneous catheter drainage). However, it is difficult to maintain a catheter-mounted state for several days, because the catheter insertion is a method of placing the catheter outside the abdominal wall, and the risk of infection increases as time passes. As the catheter insertion is an external drainage, the patient is limited in movement and feels a lot of discomfort in daily life.

As such, conventional catheters for ascites drainage are difficult to fix to a human body, cause pain and complications due to repetitive procedures, and cause discomfort to patients.

As a related art, there is Korean Patent Registration No. 10-1671612.

SUMMARY

Provided is an internal drainage catheter for ascites drainage capable of smoothly discharging ascites from a peritoneal cavity to a bladder, preventing the fluid inside the bladder from being reversed into the peritoneal cavity, increasing a fixation force to a human body, preventing pain and complications due to repetitive procedures for ascites drainage, and minimizing a patient's discomfort to enable the patient to move or make everyday life possible.

The problems of the present disclosure are not limited to the above-mentioned problems, and other problems not mentioned will be clearly understood by one of ordinary skill in the art from the descriptions below.

According to an aspect of the present invention, an internal drainage catheter for ascites drainage includes a main conduit portion passing through a bladder wall serving as a basis for separating a peritoneal cavity from a bladder, such that both ends of the main conduit portion are located at the peritoneal cavity and the bladder, respectively, the main conduit portion being formed in a tubular shape to form a flow path enabling fluid movement inside, a peritoneal cavity-side anchoring portion extending from one end of the main conduit portion and located on a side of the peritoneal cavity, the peritoneal cavity-side anchoring portion passing through the inside of a laparoscope to approach the bladder wall, while being elongated along the same axis as the main conduit portion, being wound into a ring shape by an elastic restoring force when the peritoneal cavity-side anchoring portion is separated from the inside of the laparoscope, and including an inlet via which ascites is introduced, and a bladder-side anchoring portion extending from the other end of the main conduit portion and located on a side of the bladder, the bladder-side anchoring portion passing through the inside of the laparoscope to approach the bladder wall, while being elongated along the same axis as the main conduit portion, being wound into a ring shape by an elastic restoring force when the bladder-side anchoring portion is separated from the inside of the laparoscope, including an outlet via which the ascites is discharged, and being provided with a check valve for selectively opening and closing the outlet.

The check valve may be in the form of a film of which one side is connected to a portion of the bladder-side anchoring portion adjacent to the outlet, and may have an elastic film structure provided to be elastically deformed according to a pressure due to the movement of the ascites discharged via the outlet, thereby selectively opening and closing the outlet.

The check valve may have a thickness that relatively increases toward the one side connected to the portion of the bladder-side anchoring portion adjacent to the outlet, so as to, when the ascites discharges is completed, increase a shape restoring force according to elastic deformation for closing the outlet.

The check valve may include a sealing protrusion that is formed in a convex shape to face the outlet and is fit into the outlet when the outlet is closed, so as to suppress backward inflow of fluid on the side of the bladder into the outlet and increase a closing force for the outlet.

The bladder-side anchoring portion may include an insertion groove into which a rim portion of the check valve is inserted, so as to increase adhesion with the check valve when the check valve closes the outlet.

To suppress inflow of fluid into the peritoneal cavity through the inlet, the peritoneal cavity-side anchoring portion may further include, in the inside of the peritoneal cavity-side anchoring portion where ascites flows, a peritoneal cavity-side check valve formed as a film type of which one side is connected to a portion of the peritoneal cavity-side anchoring portion adjacent to the inlet, and elastically deformed according to a pressure due to an ascites movement to selectively open and close the inlet.

In an internal drainage catheter for ascites drainage according to the present invention having a structure as described above, a main conduit portion forms a flow path inside, both ends of the main conduit portion are disposed on a peritoneal cavity and a bladder, respectively, a peritoneal cavity-side anchoring portion is positioned on the peritoneal cavity side, is wound into a ring shape by an elastic restoring force, and includes an inlet for introduction of ascites, and a bladder-side anchoring portion is wound into a ring shape by an elastic restoring force while being positioned on the bladder side, has an outlet for discharge of the ascites formed therein, and includes a check valve for selectively opening and closing the outlet, whereby the ascites may be smoothly discharged from the peritoneal cavity to the bladder, the fluid inside the bladder may be prevented from being reversed into the peritoneal cavity, a fixation force to a human body may be increased, pain and complications due to repetitive procedures for ascites drainage may be prevented, and a patient's discomfort may be minimized to enable the patient to move or make living.

The effects of the present disclosure are not limited to the above-mentioned effects, and other effects not mentioned will be clearly understood by one of ordinary skill in the art from the descriptions below.

DETAILED DESCRIPTION

An internal drainage catheter for ascites drainage according to a first embodiment of the present invention will now be described in detail with reference to the accompanying drawings.

Figure 1:
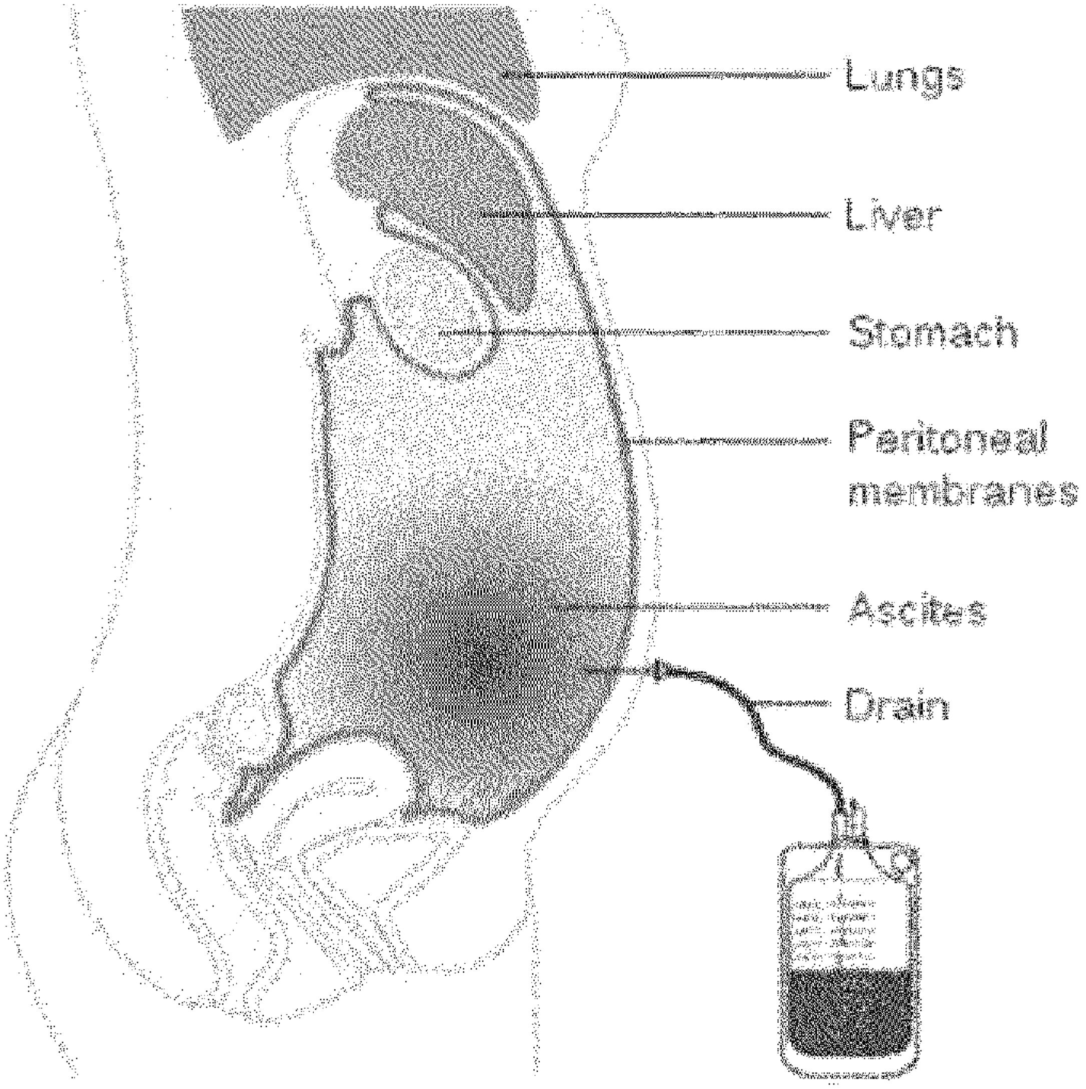
FIGS. 1 and 2 are views for explaining an ascites discharge procedure according to the related art.
Figure 2:
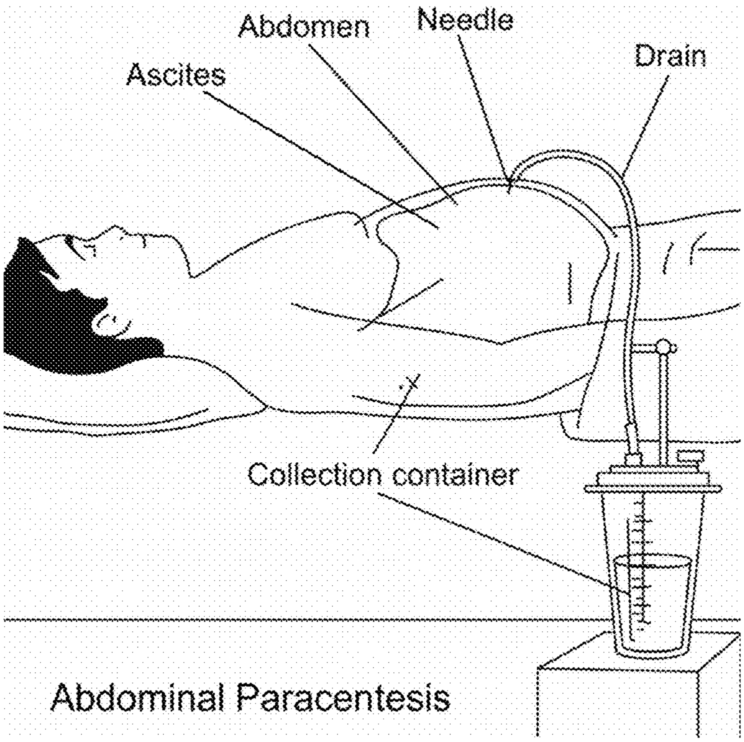
Figure 3:
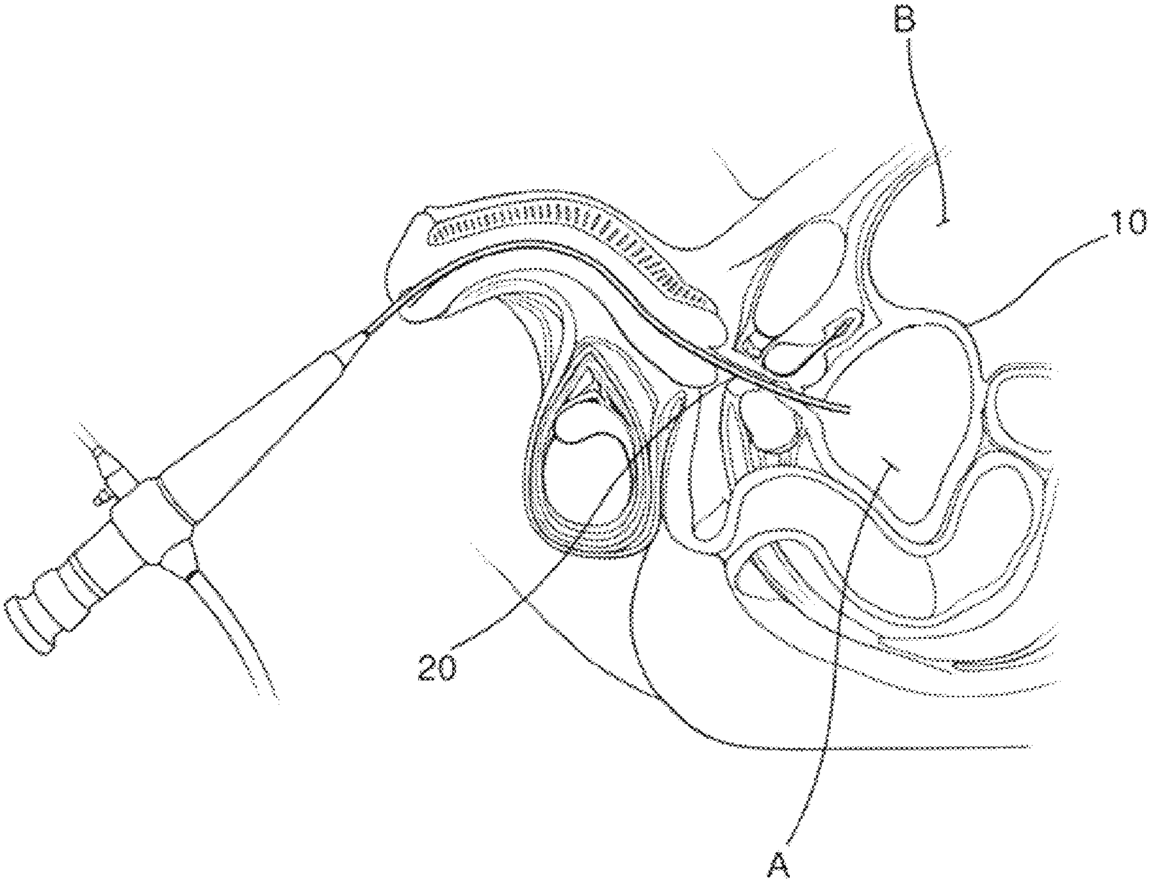
FIG. 3 is a view for explaining a procedure environment of an internal drainage catheter for ascites drainage according to a first embodiment of the present invention.
Figure 4:
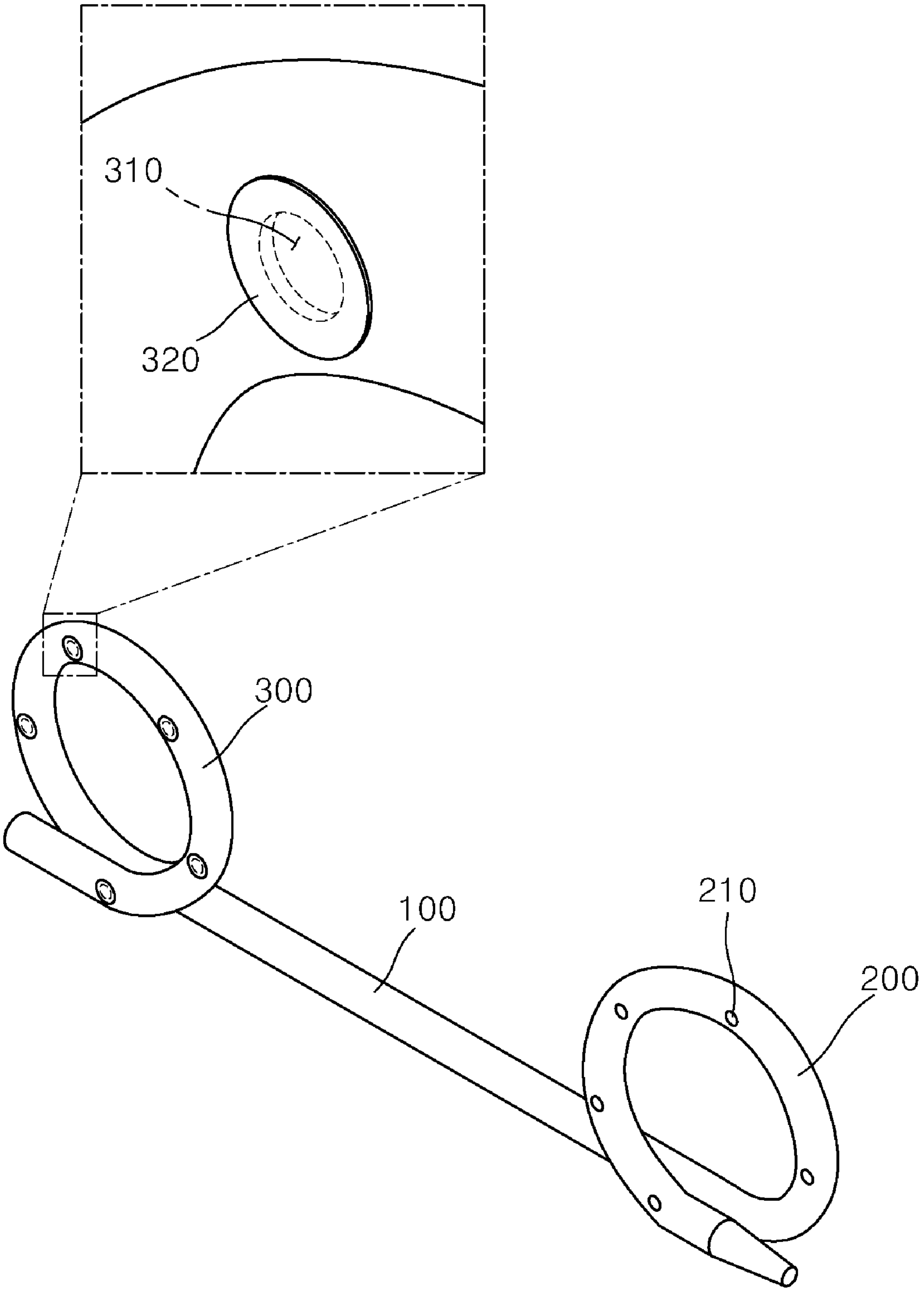
FIG. 4 is a perspective view of the first embodiment of the present invention.
Figure 5:
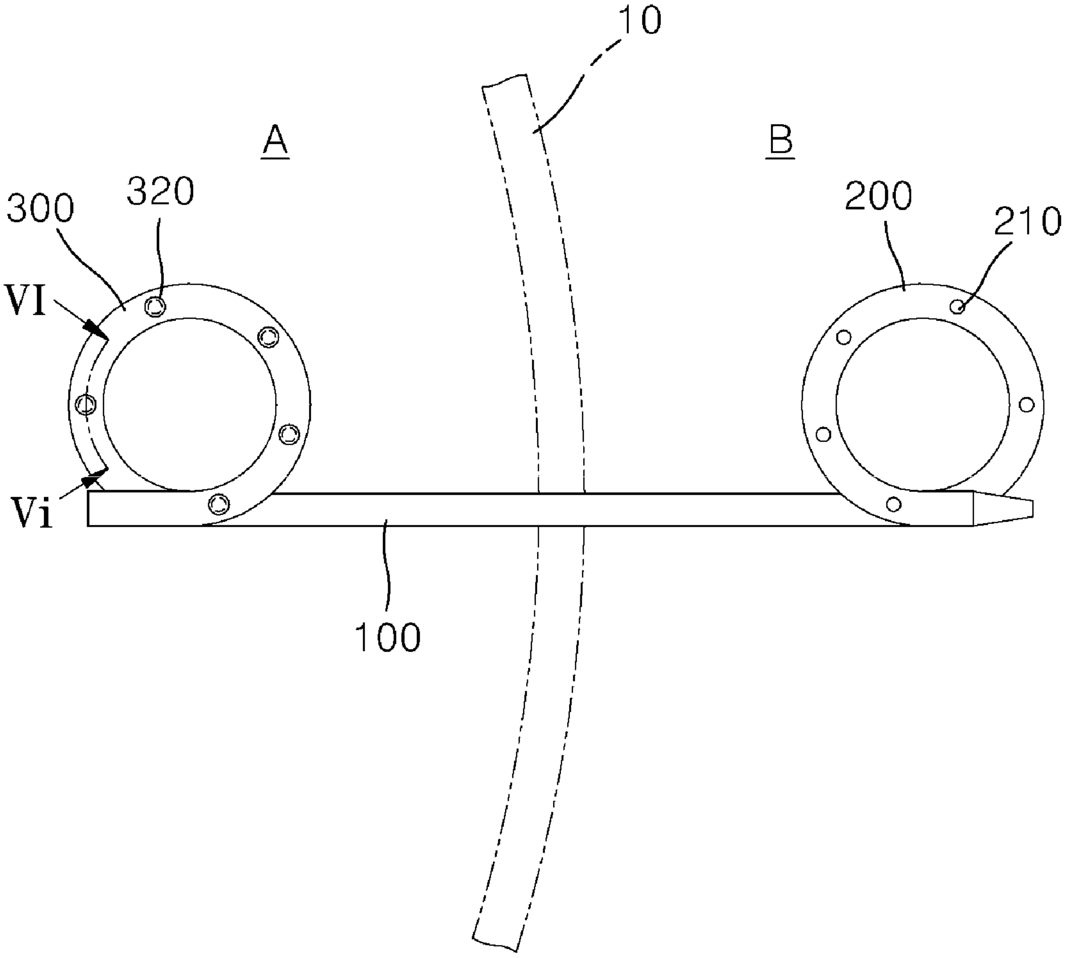
FIG. 5 illustrates a state in which a patient has undergone a procedure according to the first embodiment of the present invention.
Figure 6A:
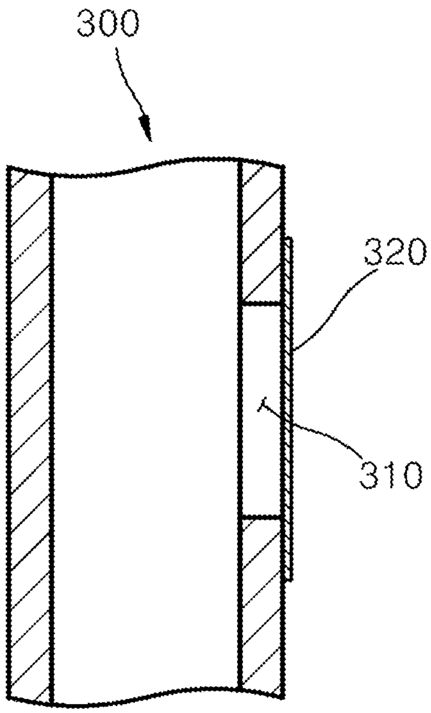
FIGS. 6A and 6B are a cross-sectional view taken along line VI-VI of FIG. for explaining a check valve provided at a position adjacent to an outlet.
Figure 6B:
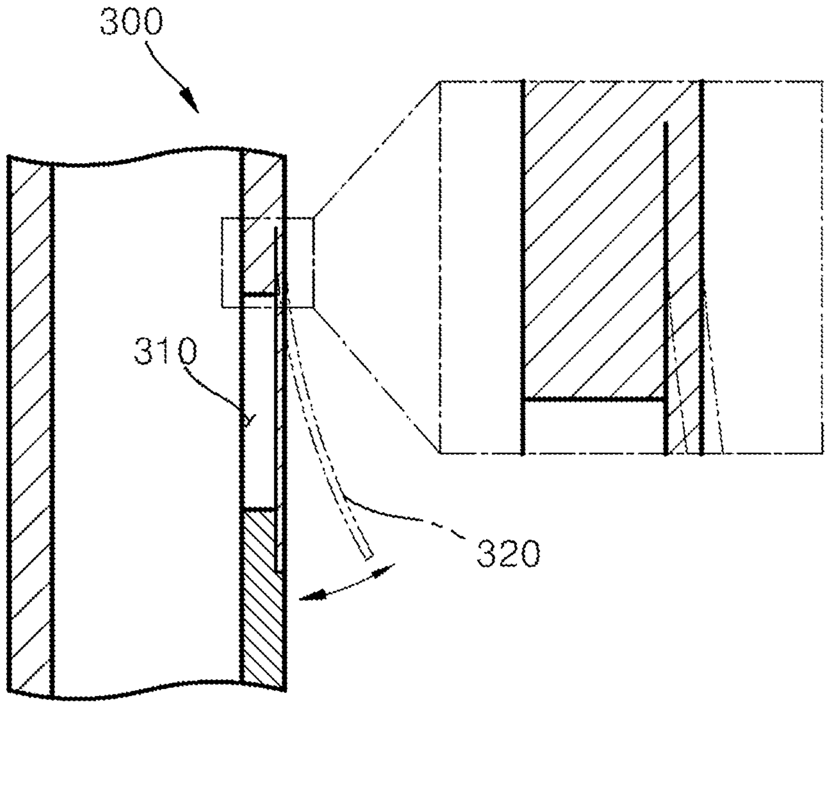
Figure 7A:
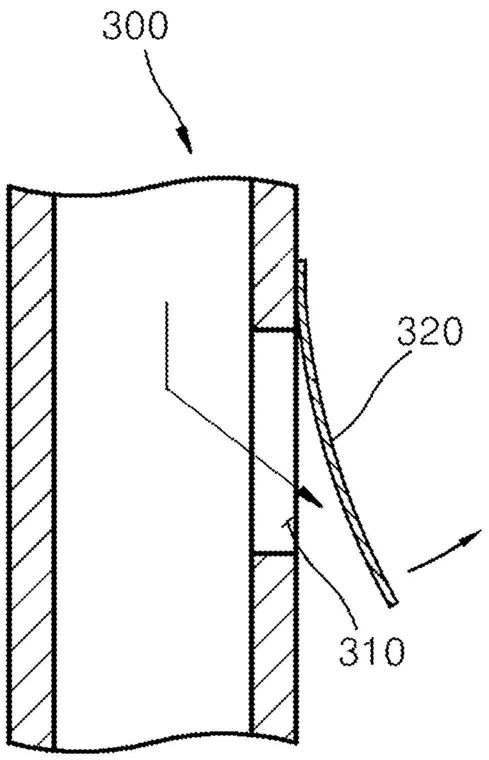
FIGS. 7A and 7B are a view for explaining the outlet opened and closed by the check valve employed in the first embodiment of the present invention.
Figure 7B:
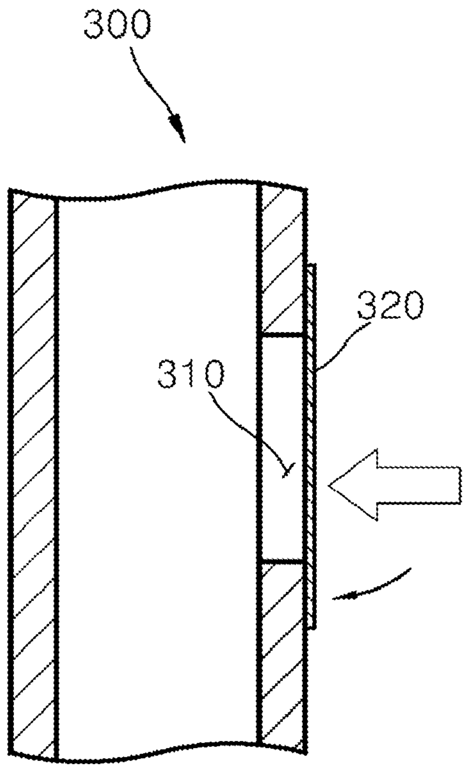

FIG. 3 is a view for explaining a procedure environment of an internal drainage catheter for ascites drainage according to a first embodiment of the present invention. FIG. 4 is a perspective view of the first embodiment of the present invention. FIG. 5 illustrates a state in which a patient has undergone a procedure according to the first embodiment of the present invention. FIGS. 6A and 6B are a cross-sectional view taken along line VI-VI of FIG. 5 for explaining a check valve provided at a position adjacent to an outlet. FIGS. 7A and 7B are a view for explaining the output opened and closed by the check valve employed in the first embodiment of the present invention.

As well shown in FIGS. 3 through 7B, the internal drainage catheter for ascites drainage according to the first embodiment of the present invention includes a main conduit portion 100, a peritoneal cavity-side anchoring portion 200, and a bladder-side anchoring portion 300.

The main conduit portion 100 is formed in a tubular shape to form a flow path enabling fluid movement inside, and passes through a bladder wall 10 serving as a basis for separating a peritoneal cavity B from a bladder A, such that both ends of the main conduit portion 100 are located at the peritoneal cavity B and the bladder A, respectively.

The main conduit portion 100 is disposed on the bladder wall 10 in a state of being separated from the inside of a laparoscope and then inserted into the bladder wall 10, so that the flow path allows the peritoneal cavity B and the bladder A to communicate with each other. Therefore, the ascites inside the peritoneal cavity B is introduced into the flow path of the main conduit portion 100 and then moved to the bladder A and discharged.

One end of the both ends of the main conduit portion 100 is connected to the peritoneal cavity-side anchoring portion 200 and is located at the peritoneal cavity, so that the ascites generated inside the peritoneal cavity may be moved to the other end of the main conduit portion 100. The other end of the both ends of the main conduit portion 100 is connected to the bladder-side anchoring portion 300 and is located at the bladder, so that the ascites moved along the flow path of the main conduit portion 100 may be discharged to the bladder.

The main conduit portion 100 may be formed of a flexible and corrosion-resistant material, and may be integrally formed with the peritoneal cavity-side anchoring portion 200 and the bladder-side anchoring portion 300.

Because the peritoneal cavity-side anchoring portion 200 extends from one end of the main conduit portion 100 and is located on the peritoneal cavity B side, the peritoneal cavity-side anchoring portion 200 passes through the inside of a laparoscope 20 to approach the bladder wall 10 while being elongated along the same axis as the main conduit portion 100. When the peritoneal cavity-side anchoring portion 200 is separated from the inside of the laparoscope 20 after approaching the bladder wall 10, the peritoneal cavity-side anchoring portion 200 is wound into a ring shape (pigtail type) by an elastic restoring force.

In addition, the peritoneal cavity-side anchoring portion 200 includes a plurality of inlets 210 connected to the flow path of the main conduit portion 100, so that the ascites inside the peritoneal cavity is introduced into the inlets 210 and moved along the flow path to the bladder-side anchoring portion 300.

The peritoneal cavity-side anchoring portion 200 is wound in a ring shape while positioned at the peritoneal cavity, to thereby prevent the peritoneal cavity-side anchoring portion 200 from escaping from the peritoneal cavity via the bladder wall 10 and prevent the main conduit portion 100 from being moved arbitrarily from the bladder wall 10.

Because the bladder-side anchoring portion 300 extends from the other end of the main conduit portion 100 and is located on the bladder A side, the bladder-side anchoring portion 300 passes through the inside of the laparoscope 20 to approach the bladder wall 10 while being elongated along the same axis as the main conduit portion 100. When the bladder-side anchoring portion 300 is separated from the inside of the laparoscope 20 after approaching the bladder wall 10, the bladder-side anchoring portion 300 is wound into a ring shape by an elastic restoring force and is positioned at the bladder A. The bladder-side anchoring portion 300 includes a plurality of outlets 310 via which the ascites is discharged.

In addition, the bladder-side anchoring portion 300 includes, adjacent to the outlets 310, check valves 320 for selectively opening and closing the outlets 310, to thereby discharge the ascites to the bladder A and prevent the fluid inside the bladder from flowing back into the main conduit portion 100 after the discharge of the ascites.

The bladder-side anchoring portion 300 is wound in a ring shape while positioned at the bladder A, to thereby prevent the bladder-side anchoring portion 300 from moving toward the peritoneal cavity via the bladder wall 10 and prevent the main conduit portion 100 from being moved arbitrarily from the bladder wall 10.

In the internal drainage catheter for ascites drainage according to the first embodiment of the present invention having such a structure, the main conduit portion 100 forms the flow path inside, the both ends of the main conduit portion 100 are disposed on the peritoneal cavity B and the bladder A, respectively, the peritoneal cavity-side anchoring portion 200 is positioned on the peritoneal cavity B side, is wound into a ring shape by an elastic restoring force, and includes the inlets 210 for introduction of the ascites, and the bladder-side anchoring portion 300 is wound into a ring shape by an elastic restoring force while being positioned on the bladder side, has the outlets 310 for discharge of the ascites formed therein, and includes the check valves 320 for selectively opening and closing the outlets 310, whereby ascites may be smoothly discharged from a peritoneal cavity to a bladder, the fluid inside the bladder may be prevented from being reversed into the peritoneal cavity, a fixation force to a human body may be increased, pain and complications due to repetitive procedures for ascites drainage may be prevented, and a patient's discomfort may be minimized to enable the patient to move or make living.

Each of the check valves 320 according to the present embodiment is in the form of a film of which one side is connected to a portion of the bladder-side anchoring portion 300 adjacent to each of the outlets 310, and has an elastic film structure provided to be elastically deformed according to a pressure due to the movement of the ascites discharged via the outlet 310, thereby selectively opening and closing the outlet 310.

In other words, when the ascites is discharged through the outlet 310, the check valve 320 is deformed by a pressure according to a movement of fluid to thereby open the outlet 310 and allow the ascites to be discharged into the bladder (see FIG. 7A). When there is no ascites movement through the outlet 310, the check valve 320 is restored in shape by a pressure inside the bladder and an elastic restoring force to thereby close the outlet 310, and derives an effect of preventing reverse inflow of the fluid inside the peritoneal cavity to the main conduit portion 100 (see FIG. 7B).

The check valve 320 may be formed of the same material as the bladder-side anchoring portion 300, and may be implemented as a separate type so that the one side may be connected to the portion adjacent to the outlet 310 in various ways (see FIG. 6A).

The one side of the check valve 320 may be integrally formed with the bladder-side anchoring portion 300, and thus may be provided on the portion of the bladder-side anchoring portion 300 adjacent to the outlet 310 (see FIG. 6B).

The internal drainage catheter for ascites drainage according to the first embodiment of the present invention has been described above. An internal drainage catheter for ascites drainage according to a second embodiment of the present invention will now be described with reference to FIG. 8.

Figure 8:
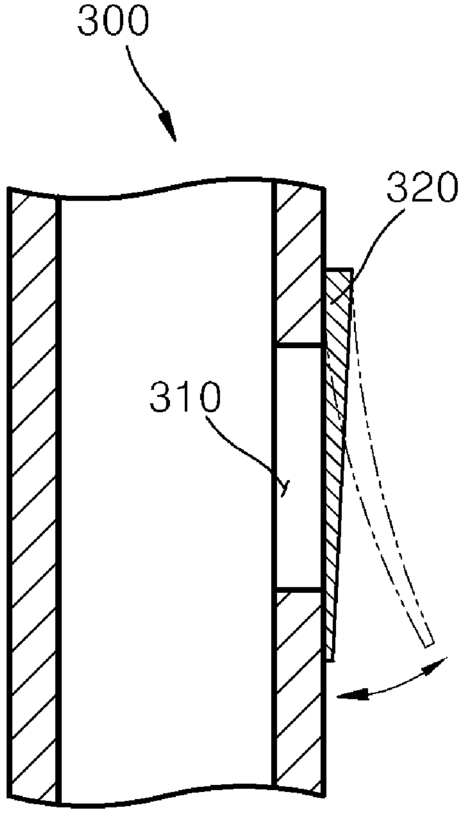
FIG. 8 is a partial cross-sectional view for explaining a check valve employed in an internal drainage catheter for ascites drainage according to a second embodiment of the present invention.

FIG. 8 is a partial cross-sectional view for explaining a check valve employed in the internal drainage catheter for ascites drainage according to the second embodiment of the present invention.

As shown in FIG. 8, the internal drainage catheter for ascites drainage according to the second embodiment of the present invention is similar to the previously described embodiment in most configurations, but there is a difference in the structure of the check valve 320.

In other words, the check valve 320 employed in the present embodiment has a thickness that relatively increases toward the one side connected to the portion of the bladder-side anchoring portion 300 adjacent to the outlet 310, and thus, when the ascites discharges is completed, may increase a shape restoring force according to elastic deformation for closing the outlet 310.

The second embodiment of the present invention has been described above. An internal drainage catheter for ascites drainage according to a third embodiment of the present invention will now be described with reference to FIGS. 9 and 10.

Figure 9:
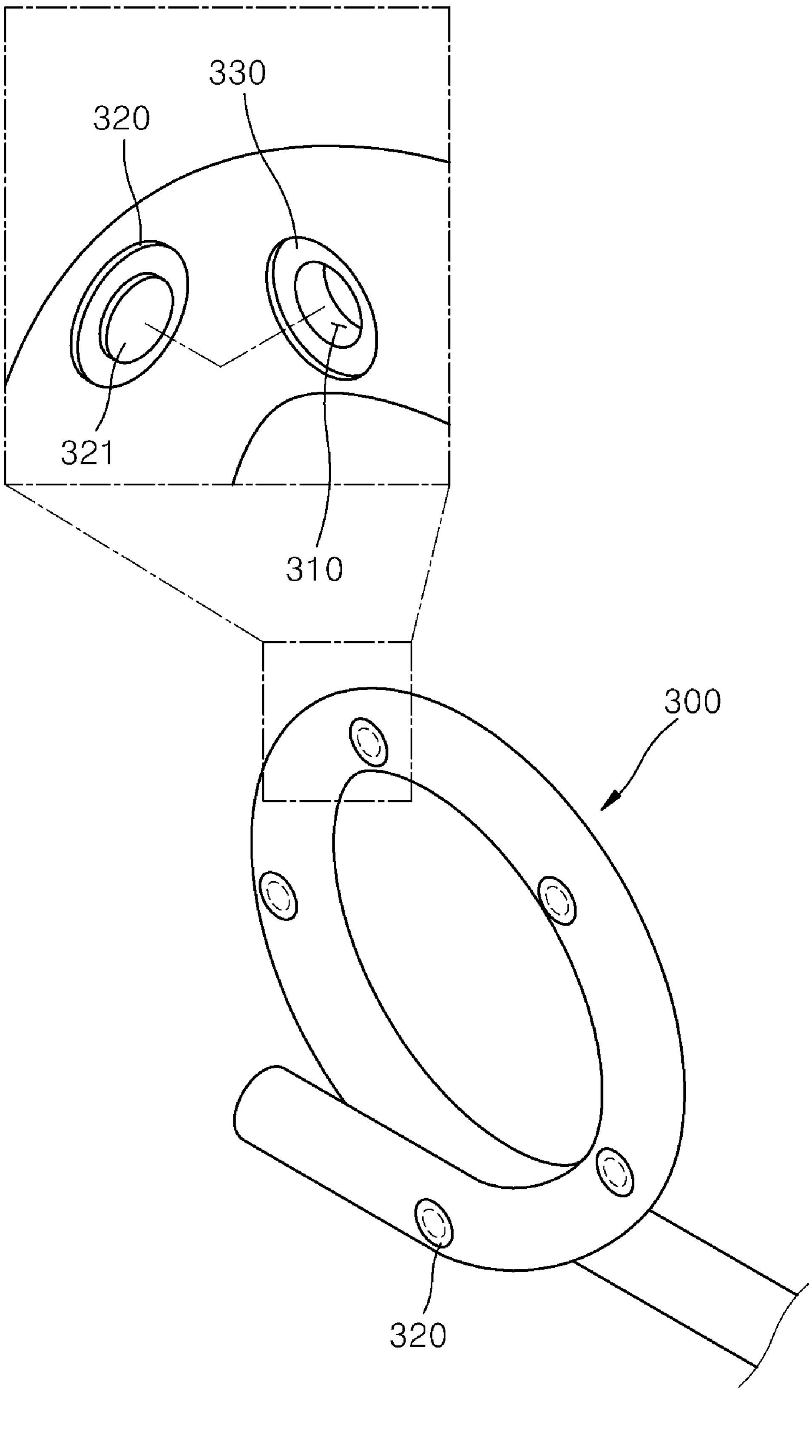
FIG. 9 is a perspective view for explaining an internal drainage catheter for ascites drainage according to a third embodiment of the present invention.
Figure 10:
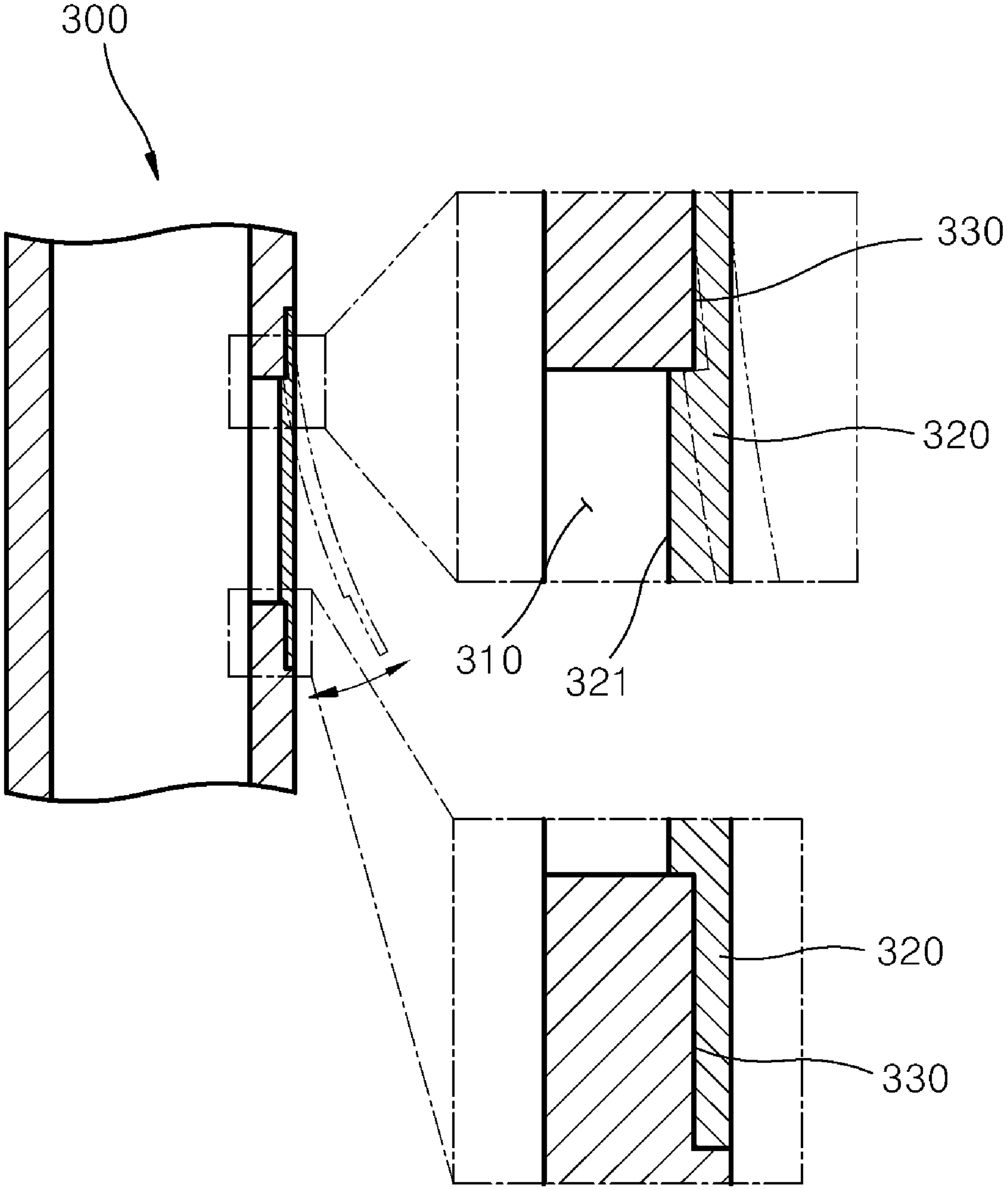
FIG. 10 is a partial cross-sectional view for explaining a check valve and an insertion groove employed in the third embodiment of the present invention.

FIG. 9 is a perspective view for explaining the internal drainage catheter for ascites drainage according to the third embodiment of the present invention, and FIG. 10 is a partial cross-sectional view for explaining a check valve and an insertion groove employed in the third embodiment of the present invention.

As shown in FIGS. 9 and 10, the internal drainage catheter for ascites drainage according to the third embodiment of the present invention is similar to the previously described embodiment in most configurations, but there is a difference in the structure of the bladder-side anchoring portion 300 and the structure of the check valve 320.

In other words, preferably, the bladder-side anchoring portion 300 employed in the present embodiment further includes an insertion groove 330. The insertion groove 330 of the bladder-side anchoring portion 300 is formed at a portion of the bladder-side anchoring portion 300 adjacent to the outlet 310, and a rim portion of the check valve 320 is inserted into and supported by the insertion groove 330, thereby deriving an effect of preventing the check valve 320 from being pushed toward the outlet 310 by a pressure inside the bladder.

The check valve 320 is connected to the bladder-side anchoring portion 300 while one side of the check valve 320 is being inserted into the insertion groove 330, and the rim portion (rim portion including the one side) of the check valve 320 is inserted into the insertion groove 330, so that, when the outlet 310 is closed, an outer surface of the bladder-side anchoring portion 300 is formed without having portions protruding from the bladder-side anchoring portion 300.

The check valve 320 according to the present embodiment may also include a sealing protrusion 321. The sealing protrusion 321 of the check valve 320 is formed in a convex shape with a size corresponding to the outlet 310 such as to face the outlet 310, and is fit into the outlet 310 when the outlet 310 is closed, thereby suppressing backward inflow of fluid on the bladder side into the outlet 310 and increasing a closing force for the outlet 310.

The third embodiment of the present invention has been described above. An internal drainage catheter for ascites drainage according to a fourth embodiment of the present invention will now be described with reference to FIG. 11.

Figure 11:
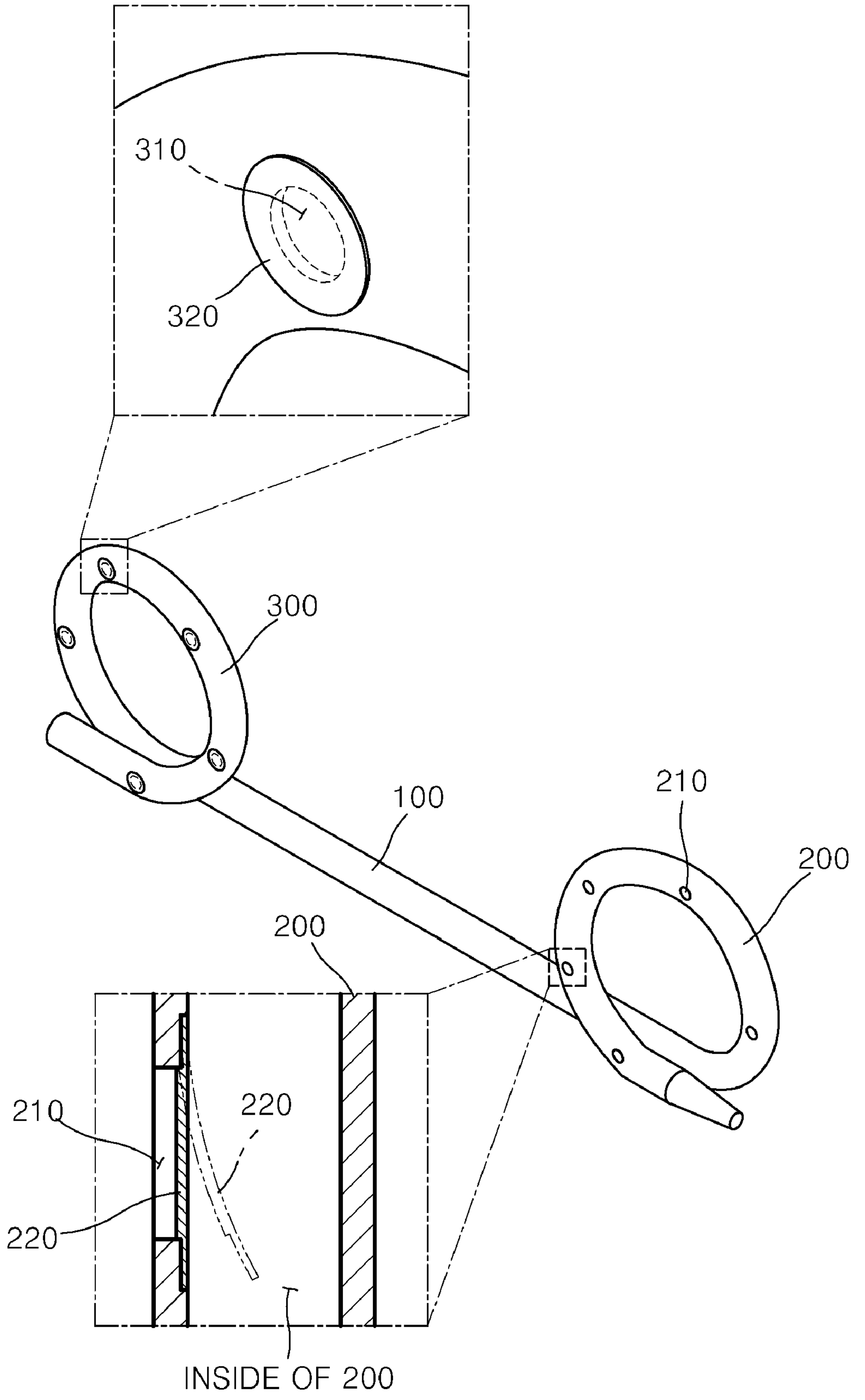
FIG. 11 is a view for explaining an internal drainage catheter for ascites drainage according to a fourth embodiment of the present invention.

FIG. 11 is a view for explaining the internal drainage catheter for ascites drainage according to the fourth embodiment of the present invention. As shown in FIG. 11, the present embodiment is similar to the previously described embodiments in most configurations, but there is a difference in the structure of the peritoneal cavity-side anchoring portion 200.

In other words, preferably, the peritoneal cavity-side anchoring portion 200 employed in the present embodiment further includes a peritoneal cavity-side check valve 220 disposed in the inside where ascites move and provided at a portion of the peritoneal cavity-side anchoring portion 200 adjacent to the inlet 210.

The peritoneal cavity-side check valve 220 is formed as an elastically-deformable film type having one side connected to the portion of the peritoneal cavity-side anchoring portion 200 adjacent to the inlet 210, so that, when ascites is introduced into the inlet 210, the peritoneal cavity-side check valve 220 is elastically deformed and thus opens the inlet 210.

When the ascites inflow into the inlet 210 is completed, the peritoneal cavity-side check valve 220 is restored in shape and closes the inlet 210 inside the peritoneal cavity-side anchoring portion 200, so that fluid on the bladder side or fluid remaining on the side of the man conduit portion 100 may be prevented from being reversed into the peritoneal cavity through the inlet 210.

The peritoneal cavity-side check valve 220 may increase the closing force of the inlet 210 by including the sealing protrusion employed in the above-described third embodiment at a position corresponding to the inlet 210. In addition, the peritoneal cavity-side anchoring portion 200 includes an insertion groove which is formed at the portion of the peritoneal cavity-side anchoring portion 200 adjacent to the inlet 210 and into which a rim portion of the peritoneal cavity-side check valve 220 is inserted, thereby increasing adhesion between the peritoneal cavity-side check valve 220 and the peritoneal cavity-side anchoring portion 200.

Although preferred embodiments of the present invention have been described, the present invention is not limited to the embodiments described above, but is defined by the claims, and it is apparent that various modifications and developments can be made in the technical field to which the present invention belongs.

What is claimed is:

1. An internal drainage catheter for ascites drainage, comprising:

a main conduit portion configured for passing through a bladder wall serving as a basis for separating a peritoneal cavity from a bladder, such that both ends of the main conduit portion are configured to be located at the peritoneal cavity and the bladder, respectively, the main conduit portion being formed in a tubular shape to form a flow path enabling fluid movement inside;

a peritoneal cavity-side anchoring portion extending from one end of the main conduit portion, the peritoneal cavity-side anchoring portion configured to be located on a side of the peritoneal cavity, the peritoneal cavity-side anchoring portion configured for passing through the inside of a laparoscope to approach the bladder wall, while being elongated along the same axis as the main conduit portion, being wound into a ring shape by an elastic restoring force when the peritoneal cavity-side anchoring portion is separated from the inside of the laparoscope, the peritoneal cavity-side anchoring portion including an inlet via which ascites is introduced; and a bladder-side anchoring portion extending from the other end of the main conduit portion, the bladder-side anchoring portion configured to be located on a side of the bladder, the bladder-side anchoring portion configured for passing through the inside of the laparoscope to approach the bladder wall, while being elongated along the same axis as the main conduit portion, being wound into a ring shape by an elastic restoring force when the bladder-side anchoring portion is separated from the inside of the laparoscope, including an outlet via which the ascites is discharged, the bladder-side anchoring portion provided with a check valve for selectively opening and closing the outlet, wherein the check valve is in the form of a film of which one side is connected to a portion of the bladder-side anchoring portion adjacent to the outlet, and has an elastic film structure provided to be elastically deformed according to a pressure due to the movement of the ascites discharged via the outlet, thereby selectively opening and closing the outlet.

2. The internal drainage catheter for ascites drainage of claim 1, wherein the check valve has a thickness that relatively increases toward the one side connected to the portion of the bladder-side anchoring portion adjacent to the outlet, so as to, when the ascites discharges is completed, increase a shape restoring force according to elastic deformation for closing the outlet.

3. The internal drainage catheter for ascites drainage of claim 1, wherein the check valve includes a sealing protrusion that is formed in a convex shape to face the outlet and is fit into the outlet when the outlet is closed, so as to suppress backward inflow of fluid on the side of the bladder into the outlet and increase a closing force for the outlet.

4. The internal drainage catheter for ascites drainage of claim 1, wherein the bladder-side anchoring portion includes an insertion groove into which a rim portion of the check valve is inserted, so as to increase adhesion with the check valve when the check valve closes the outlet.

5. The internal drainage catheter for ascites drainage of claim 1, wherein, to suppress inflow of fluid into the peritoneal cavity through the inlet, the peritoneal cavity-side anchoring portion further includes, in the inside of the peritoneal cavity-side anchoring portion where ascites flows, a peritoneal cavity-side check valve formed as a film type of which one side is connected to a portion of the peritoneal cavity-side anchoring portion adjacent to the inlet, and elastically deformed according to a pressure due to an ascites movement to selectively open and close the inlet.

* * * * *